United States Patent [19]

Takasa et al.

[11] 4,357,276

[45] Nov. 2, 1982

[54] PROCESS FOR SEPARATION OF INDOLE USING X AND Y TYPE ZEOLITES

[75] Inventors: Kenji Takasa, Yokohama; Keizo Hirakawa, Tokyo; Hiroji Nishimaru, Kawasaki; Makoto Honda, Tokyo, all of Japan

[73] Assignee: Asahi Kasei Kogyo Kabushiki Kaisha, Osaka, Japan

[21] Appl. No.: 197,459

[22] Filed: Oct. 16, 1980

[30] Foreign Application Priority Data

Nov. 2, 1979 [JP] Japan ................................. 54-141215
Feb. 8, 1980 [JP] Japan ................................. 55-13532

[51] Int. Cl.³ .................. C07D 209/08; C07D 209/06
[52] U.S. Cl. ................................ 260/319.1; 260/708;
252/454; 252/457; 252/459; 252/455 Z
[58] Field of Search ........................... 260/319.1, 708

[56] References Cited

U.S. PATENT DOCUMENTS 3,005,826 10/1961 Fleck et al. ........................ 260/708
3,159,632 12/1964 Sargent et al. ................. 260/708 X

*Primary Examiner*—David B. Springer
*Attorney, Agent, or Firm*—Sprung, Horn, Kramer & Woods

[57] ABSTRACT

A process for separating indole from a mixture of indole with at least one hydrocarbon or its derivative which comprises the steps of contacting the mixture with a faujasite structured zeolite to selectively adsorb indole on the zeolite and contacting a desorbent A selected from the group consisting of $C_{2-10}$ aliphatic or $C_{7-10}$ aromatic ether compounds, $C_{2-10}$ aliphatic ester compounds and $C_{3-10}$ aliphatic ketone compounds with the indole-adsorbed zeolite to separate indole and the process which comprises, in addition, the step of contacting at least one desorbent B of the formula,

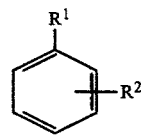

wherein
$R^1$ is a $C_{1-3}$ alkyl group, and
$R^2$ is a hydrogen atom or a $C_{1-3}$ alkyl group, with the indole-adsorbed zeolite prior to the contact of the desorbent A with the indole-adsorbed zeolite.

12 Claims, 16 Drawing Figures

PROCESS FOR SEPARATION OF INDOLE USING X AND Y TYPE ZEOLITES

BACKGROUND OF THE INVENTION

1. Field of the Invention

This invention relates to a process for the adsorption separation of indole from a mixture of indole with at least one hydrocarbon or a derivative thereof by a zeolite.

2. Description of the Prior Art

Indole is a useful starting material for perfumes, dyes and pharmaceuticals and has recently been spotlighted as a starting material for preparing essential amino acids. Indole is found in coal tar, jasmine oil, neroli oil and putrid protein. Of these substances, coal tar which is produced in a large amount industrially contains 0.2 to 0.5% by weight of indole and a distillate having a boiling point of 220° C. to 270° C. which is obtained by distilling coal tar is said to contain 1.5 to 4.5% by weight of indole.

As the known process for separating indole from coal tar, firstly the acid component and the base component are removed from the distillate having a boiling point of 220° C. to 270° C. obtained by distilling coal tar and secondly the remaining oily substance is heated with sodium or sodium amide at a temperature of 100° C. to 125° C. or with potassium hydroxide at 200° C. to 250° C. to isolate indole sodium or indole potassium. This process requires not only plural steps but also expensive sodium or sodium amide and moreover, the procedures are complicated. As a result, this process can hardly be said to be efficient. In another process, the distillate from which the acid component and the base component have been removed is repeatedly subjected to fractional crystallization at a temperature of −20° C. to +25° C. to remove mainly naphthalene and 2-methylnaphthalene, and its mother liquor is subjected to rectification to separate crude indole, followed by recrystallizing the crude indole from petroleum ether. This process requires plural steps and rectification of high boiling point substances and thus, a large amount of energy is disadvantageously necessary. Also Koks Khim 4, 34 to 37 (1978) describes the separation of indole from a distillate of coal tar containing indole by gas chromatography. This process which does not require complicated procedures is excellent in simply obtaining indole but the starting material must be gasified and also the temperature of the column must be maintained at a temperature of 200° C. to 300° C. As the disadvantages of this process, not only a large amount of energy is necessary but also the apparatus becomes remarkably large in handling gaseous substances. Thus, this process is not suitable for handling a large amount of the starting materials. Thus, the conventional process for separating indole from coal tar is troublesome and not efficient.

It has now been found that in separating indole from its mixture with at least one hydrocarbon or a derivative thereof, indole can be easily and efficiently separated by contacting the mixture with a faujasite structured zeolite. More specifically, when the mixture as such or a solution of the mixture dissolved in an appropriate solvent other than a desorbent A as defined below is contacted to the zeolite, each substance of the mixture is adsorbed on the zeolite but the adsorbability to the zeolite is different among indole and substances other than indole and as a result, the composition of the zeolite phase becomes rich in indole. Thus indole can be separated and recovered by replacing the indole in the zeolite phase by an appropriate desorbent.

SUMMARY OF THE INVENTION

Accordingly, the present invention in one embodiment provides a process for separating indole from a mixture of indole with at least one hydrocarbon or its derivative which comprises the steps of contacting the mixture with a faujasite structured zeolite to selectively adsorbe indole on the zeolite and contacting a desorbent A selected from the group consisting of $C_{2-10}$ aliphatic or $C_{7-10}$ aromatic ether compounds, $C_{2-10}$ aliphatic ester compounds and $C_{3-10}$ aliphatic ketone compounds with the indole-adsorbed zeolite to separate indole.

The present invention in another embodiment provides a process for separating indole from a mixture of indole with at least one hydrocarbon or its derivative which comprises the steps of contacting the mixture with a faujasite structured zeolite to selectively adsorbe indole on the zeolite, contacting a desorbent B of the formula,

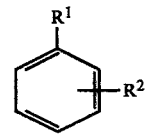

wherein
$R^1$ is a $C_{1-3}$ alkyl group, and
$R^2$ is a hydrogen atom or a $C_{1-3}$ alkyl group,
with the indole-adsorbed zeolite and contacting the desorbent A as described above with the indole-adsorbed zeolite to desorbe indole.

DETAILED DESCRIPTION OF THE INVENTION

Figure 1:
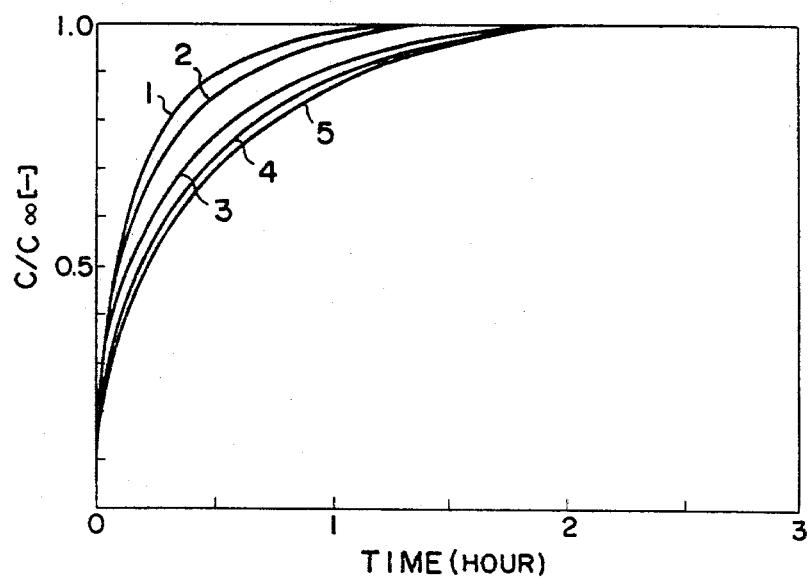
FIGS. 1 and 2 illustrate the amount of indole adsorbed with the passage of time with the X type and Y type zeolite whose exchangeable ions have been replaced by lithium, sodium, potassium, rubidium or cesium, respectively.

The zeolites which can be employed in this invention are any faujasite structured zeolites. The faujasite structured zeolites are crystalline aluminosilicates having a 6-rings structure and a poly-hedral cage of β, 26-hedron, classified in Group 4 by the crystalline structure including natural faujasites, synthetic X type zeolites and synthetic Y type zeolites. Of these zeolites, synthetic X type zeolites and synthetic Y type zeolites are preferred since they are industrially produced in large amounts and can be easily and readily available.

The synthetic X type zeolite has a typical oxide formula $Na_2O.Al_2O_3.2.5\ SiO_2.6H_2O$; a typical unit-cell formula $Na_{86}[(AlO_2)_{86}(SiO_2)_{106}].264H_2O$; the density 1.93 g/cc; the unit-cell constant 25.02~24.86 Å; the void volume 0.50 cc/cc; the free aperture 2.2 Å (6- membered ring), 7.4 Å (12-membered ring); and the kinetic diameter 8.1 Å.

The synthetic Y type zeolite has a typical oxide formula $Na_2O.Al_2O_3.4.8SiO_2.8.9H_2O$; a typical unit-cell formula $Na_{56}[(AlO_2)_{56}(SiO_2)_{136}].250.H_2O$; the density 1.92 g/cc; the unit-cell constant 24.85~24.61 Å; the void volume 0.48 cc/cc; the free aperture 2.2 Å (6-membered ring), 7.4 Å (12-membered ring); the the kinetic diameter 8.1 Å.

All or part of the exchangeable sodium ion sites of the synthetic X type zeolite and Y type zeolite can be replaced with at least one cation such as a metal ion, hydrogen ion and ammonium ion. Of these cations, a metal ion is preferred.

Exemplary metal ions include metals of the Ia group of the Periodic Table such as lithium, sodium, potassium, rubidium and cesium; metal ion of the IIa group of the Periodic Table such as magnesium, calcium, strontium and barium; metal ions of the Ib group of the Periodic Table such as copper and silver; metal ion of the IIb group of zinc and cadmium; metal ions of the VIII group of the Periodic Table such as iron, nickel and cobalt; rare earth metal ions such as yttrium, lanthanum and cerium; and any combinations of these metal ions. In case of a sodium type zeolite all or part of the sodium ions can be replaced.

Of these metal ions, the metal ions of the Ia group of the Periodic Table are preferred since indole is adsorbed on the ion exchanged X type or Y type zeolite with a high selectivity and indole does not undergo any change in quality. The term "change in quality" means that part of indole which has been irreversibly adsorbed on the zeolite with unknown reason cannot be desorbed by a desorbent having a suitably strong desorbability such as acetonitrile and remains adsorbed on the zeolite. The extent of the change in quality is shown by the rate of desorption of indole as will be defined below.

The ion exchange of the faujasite structured zeolite with a desired cation or cations is conducted by contacting the zeolite with an aqueous solution of soluble salts of the cation or cations desired to be exchanged onto the zeolite. The soluble salts include inorganic salts such as chlorides, nitrates, sulfates and carbonates and organic salts such as acetates. Or the zeolite is contacted with a solution of an inorganic acid such as hydrochloric acid, nitric acid and sulfuric acid in which is dissolved at least one compound capable of forming cation or cations desired to be exchanged onto the zeolite. The compounds include metals, oxides and hydroxides. The ion exchange may be conducted batchwise or continuously. The amount of the cation or cations exchanged onto the zeolite is at least 0.8 equivalent of the exchangeable cation of the zeolite. The ion concentration of the soluble salts in an aqueous solution for the ion exchange is appropriately selected below the saturation and is typically about 0.01 N to about 2 N below the saturation. The temperature of ion exchange is typically about 0° C. to 98° C., but in order to increase the rate of ion exchange, a comparatively high temperature is preferred. The conventional procedures of ion exchange as described in Japanese Pat. Nos. 6713/1957, 618/1958 and 5523/1958 may be employed in this invention.

The mixture of indole which can be employed in the adsorption separation of indole in this invention is any mixture of indole with a hydrocarbon and/or a derivative thereof and, more particularly, the mixture of indole with at least one compound selected from the group consisting of $C_{6-22}$ linear and cyclic hydrocarbons and $C_{4-20}$ linear and cyclic ethers, $C_{4-20}$ esters, $C_{4-20}$ ketones, $C_{4-20}$ thioethers and $C_{4-20}$ thioesters. Exemplary mixtures include mixtures of indole with at least one compound selected from the group consisting of naphthalene, thionaphthalene, 1-methylnaphthalene, 2-methylnaphthalene, biphenyl, 1,5-dimethylnaphthene, 1,7-dimethylnaphthalene, 2,6-dimethylnaphthalene, acenaphthene, diphenylene oxide and fluorene. As such mixtures which can be easily available industrially, there are distillate of coal tar. Especially, a distillate having a boiling point of 220° C. to 270° C. obtained by distilling coal tar contains a comparatively large amount of indole. A preferred mixture of indole which can be employed in this invention is a distillate of coal tar having a boiling point of 220° C. to 270° C. and comprises, in addition to indole, naphthalene, thionaphthene, 1-methylnaphthalene, 2-methylnaphthalene, biphenyl, 1,5-dimethylnaphthalene, 1,7-dimethylnaphthalene, 2,6-dimethylnaphthalene, acenaphthene, diphenylene oxide and fluorene in any ratio. The composition of the distillate varies depending upon the origin of coal and the distillation conditions for obtaining an indole-containing distillate by distillation of coal. In this invention distillates having any composition can be employed. When the mixtures of indole comprise a large amount of a basic substance such as pyridine, a pyridine derivative, quinoline and a quinoline derivative or an acidic substance such as phenol and xylenols, the adsorbability of the zeolite is decreased and the life of the zeolite for repeated use is shortened. Accordingly, it is preferred to remove these basic or acidic substances from the distillate of coal tar. The basic substances can be easily removed by washing the distillate of coal tar with a suitable inorganic acid such as sulfuric acid (concentration, about 1 to about 30% by weight). When sulfuric acid of at least 30% by weight is employed, the loss of indole due to its polymerization increases disadvantageously. Also the acidic substances can be easily removed by washing the distillate of coal tar with a suitable inorganic base such as about 1 to about 30% by weight aqueous sodium hydroxide solution.

When the mixtures of indole to be separated contain water, the adsorbability of the zeolite is decreased and the life of the zeolite for repeated use is shortened. Accordingly, it is preferred to remove water from the mixtures of indole.

The selectivity of a system comprising an adsorbent and a solution comprising substances A′ and B′ in an equilibrium state for one substance A′ over another substance B′ is denoted by the formula, $$K_{A'}^{B} = \frac{Y_{B}/Y_{A'}}{X_{B'}/X_{A'}}$$

wherein
$X_{A'}$ represents a concentration of substance A′ in the external solution adjacent to the adsorbent,
$X_{B'}$ represents a concentration of substance B′ in the external solution adjacent to the adsorbent,
$X_{A'}$ represents a concentration of substance A′ in the adsorbent phase,
$Y_{B'}$ represents a concentration of substance B′ in the adsorbent.
For example, $K_{desorbent\,A}^{indole}$ denotes a selectivity of an adsorbent for indole over a desorbent A. The selectivity is an index for the separation capacity of an adsorbent. When the adsorbability of substance B′ is stronger than that of substance A', the separability of an adsorbent becomes higher with increased selectivities $K_{A'}{}^{B'}$.

In general, in conducting the adsorption separation, adsorbents which are considered excellent have a high selectivity and a high adsorption capacity in an equilibrium state and do not cause the change in quality of the substances to be separated and, in addition, have high adsorption and desorption velocities for the substances to be separated. For example, with an desorbent having low adsorption and desorption velocities employed, the degree of tailing of the substances to be separated is increased and as a result, a desired substance cannot be efficiently separated.

It has now been found that the adsorption and desorption velocities of an adsorbent for indole greatly vary depending upon the kind of the adsorbent employed. More specifically, the adsorption and desorption velocities of an adsorbent are the highest with a lithium ion-replaced Y type zeolite of the faujasite structured zeolites which can be employed in this invention and the second highest with a sodium ion-replaced Y type zeolite. In this invention the lithium ion-replaced Y type zeolite is a more preferred adsorbent since indole is adsorbed thereon with a high selectivity and at the same time no change in quality of indole is observed in addition to its high adsorption velocity. In this invention the sodium ion-replaced Y type zeolite is also preferably employed without any substantial problem although its adsorption velocity is slightly inferior to the adsorption velocity of the lithium-ion replaced zeolite.

The desorbent A which can be employed in this invention is required to have an appropriate boiling point and to dissolve each of the substances to be separated and further to have an appropriate adsorbability to an adsorbent. It is preferred that the desorbent A has the following range of $K_{desorbent\ A}{}^{indole}$, $$0.1 \leq K_{desorbent\ A}{}^{indole} \leq 10$$

When $K_{desorbent\ A}{}^{indole}$ is lower than 0.1, the adsorbability of the desorbent A to an adsorbent is too strong and indole cannot be adsorbed on the adsorbent sufficiently and passes the adsorbent when the indole mixture to be separated is contacted with the adsorbent. On the other hand, when $K_{desorbent\ A}{}^{indole}$ is higher than 10, a large amount of the desorbent A is necessary due to the weak desorbability of indole and thus indole is disadvantageously diluted to a great extent.

The desorbents A which satisfy the above described range of $K_{desorbent\ A}{}^{indole}$ include $C_{2-10}$ aliphatic or $C_{7-10}$ aromatic ether compounds, $C_{2-10}$ aliphatic ester compounds and $C_{3-10}$ aliphatic ketone compounds.

Exemplary desorbents A include diethyl ether, di-n-propyl ether, isopropyl ether, methyl n-butyl ether, ethyl n-butyl ether, di-n-butyl ether, anisole, ethyl acetate, n-propyl acetate, n-butyl acetate, n-amyl acetate, isobutyl acetate, tert-butyl acetate, isoamyl acetate, methyl propionate, ethyl propionate, di-n-propyl ketone, methyl ethyl ketone, methyl isobutyl ketone, 2-pentanone, 2-heptanone, 2-octanone and cyclohexanone.

Of these compounds, it is preferred to employ a desorbent A which has the following range of $K_{desorbent\ A}{}^{indole}$ $$0.8 \leq K_{desorbent\ A}{}^{indole} \leq 3.0$$

and which does not cause any change in quality of indole even in the case of its repeating use in a continuous separation operation. As such a desorbent A, anisole is more preferred. In this invention, methyl ethyl ketone, methyl isobutyl ketone, 2-octanone and cyclohexanone are also preferably employed without any substantial problem even the change in quality of indole is slightly observed.

The adsorption separation of the mixture of indole with a hydrocarbon and/or a derivative thereof using a faujasite structured zeolite in this invention can be conducted by any method comprising contacting the mixture with the zeolite batchwise or continuously.

The batchwise operation comprises repeating the steps of feeding a mixture containing indole, if desired or if necessary, in the form of a solution of a suitable solvent to a separator having a faujasite structured zeolite packed zone to form an indole mixture adsorption zone, feeding a desorbent A to the separator to desorbe the adsorbed substance and collecting the entire amount of the components of the mixture.

The continuous operation can be carried out, for example, according to U.S. Pat. No. 2,985,589. This operation will be explained with a mixture of 1-methylnaphthalene and indole to be separated.

To one end of a developing column packed with a faujasite structured zeolite to a desired length is fed a desorbent A, and the desorbent A flowed from the other end of the column is returned to the column, resulting in a circulation of the desorbent A. Then the mixture of 1-methylnaphthalene and indole is fed to the column at an appropriate position of the column to form a mixture adsorption zone. The mixture adsorption zone migrates in the flow direction of the desorbent A as a whole by the desorbent A following in the rear. Within the mixture adsorption zone 1-methylnaphthalene and indole are repeatedly adsorbed on and desorbed from the zeolite, respectively, and since the zeolite phase is richer in indole having a stronger adsorbability than the external liquid phase adjacent to the zeolite phase, 1-methylnaphthalene having a weaker adsorbability advances relatively faster in the flow direction of the desorbent A, resulting in the separation of indole from 1-methylnaphthalene. According to the migration of the mixture adsorption zone the inlet for the starting mixture is moved to an appropriate position of the mixture adsorption zone and a portion rich in 1-methylnaphthalene and a portion rich in indole are withdrawn from an appropriate frontal position and an appropriate rear position of the mixture adsorption zone, respectively, and the recovered amount of the indole mixture is fed to the separator at an appropriate position outside the mixture adsorption zone, resulting in a stationary state of the separation system. In general, it is difficult to continuously move an inlet for the indole mixture and the desorbent A and an outlet for the portions rich in 1-methylnaphthalene and indole in the mixed adsorption zone and accordingly, the developing column is partitioned into a plurality of sections and each section is provided with an inlet and an outlet which are periodically used for the indole mixture, the desorbent A, the portions rich in 1-methylnaphthalene and indole, resulting in an approximately stationary state of the separation system.

In carrying out the batchwise operation with a distillate whose boiling point is 220° C. to 270° C. obtained by distilling coal tar and whose indole content is as low as 1.5 to 4.5% by weight, the effluent curves for indole and substances other than indole such as naphthalene and methylnaphthalenes whose adsorbabilities to an adsorbent are weaker than the adsorbability of indole overlap one another in their tails. As a result, the fractions rich in indole contain a large amount of substances other than indole. In order to obtain indole at a high concentration in this operation, a large amount of an adsorbent based on the amount of the indole mixture to be separated may be employed or the batchwise operation is repeated by using the fractions rich in indole as the indole mixture to be separated. Another process which can be preferably employed in this invention comprises contacting the indole mixture with a faujasite structured zeolite to selectively adsorb indole on the zeolite, contacting a desorbent B having an appropriate adsorbability to the zeolite with the indole-adsorbed zeolite to desorbe substances other than indole having a weaker adsorbability and to leave most of indole in the zeolite phase and contacting a desorbent A as described above with the indole-adsorbed zeolite to desorbe the indole in the zeolite phase whereby recovering indole of a high purity.

The above described desorbent B which can leave most of the indole in the zeolite phase and desorbe substances other than indole having a weaker adsorbability to the zeolite from the zeolite phase is represented by the formula,

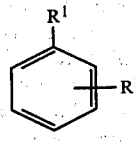

wherein
$R^1$ is a $C_{1-3}$ alkyl group and
$R^2$ is a hydrogen atom or a $C_{1-3}$ alkyl group.

Exemplary desorbents B include toluene, ethylbenzene, o-xylene, m-xylene, p-xylene, isopropylbenzene and any mixtures thereof.

These desorbents B have appropriate boiling points and can be easily separated from the indole mixture to be separated and the desorbents A by the conventional method such as distillation. Further, the desorbents B can easily dissolve the indole mixture to be separated and the desorbents A and do not cause the change in quality of the zeolite and indole nor undergo the change of quality by themselves even when they are repeated used.

In carrying out the adsorption separation of the indole mixture, the amounts of the indole mixture and the desorbents A and B based on the amount of the faujasite structured zeolite are suitably selected. A preferred relationship between the weight of the indole mixture and the weight of the zeolite is denoted by the equation;

$$\frac{0.5\ W_1}{X} \leq W_2 \leq \frac{5\ W_1}{X}$$

wherein
$W_1$ is the weight of the zeolite;
$W_2$ is the weight of the indole mixture,
X is the percent by weight of indole present in the indole mixture.

When $W_2$ is greater than $(5\ W_1)/X$, the desorption of indole by the desorbent B becomes remarkable disadvantageously. On the other hand, when $W_2$ is smaller than $(0.5\ W_1)/X$, the separation efficiency is decreased.

A more preferred relationship is denoted by the equation;

$$W_1/X \leq W_2 \leq (3.5\ W_1)/X$$

A preferred relationship between the weight of the desorbent B and the weight of the zeolite is denoted by the equation;

$$0.1\ W_1 \leq W_3 \leq 3.0\ W_1$$

wherein
$W_1$ is the same as define above,
$W_3$ is the weight of the desorbent B.

When $W_3$ is greater than $3.0\ W_1$, the desorption of indole by the desorbent B becomes great. On the other hand, when $W_3$ is smaller than $0.1\ W_1$, the purity of indole does not increase. A more preferred relationship is denoted by the equation;

$$0.3\ W_1 \leq W_3 \leq 1.5\ W_1$$

Also a preferred relationship between the weight of the desorbent A and the weight of the zeolite is denoted by the equation;

$$0.1\ W_1 \leq W_4$$

wherein
$W_1$ is the same as defined above,
$W_4$ is the weight of the desorbent A.

When $W_4$ is smaller than $0.1\ W_1$, the desorption of indole is not sufficient and as a result, the loss of indole is increased. The upper amount of $W_4$ is not particularly limited but if it is too large, indole is excessively diluted. A more preferred relationship is denoted by the equation;

$$0.3\ W_1 \leq W_4 \leq 1.5\ W_1$$

The temperature of contacting the indole mixture, the desorbent A and the desorbent B with the faujasite structured zeolite which can be employed in this invention varies depending upon the kind of the zeolite selected, the properties of the indole mixture chosen such as the melting point, the boiling point and the viscosity and the kind of the desorbents A and B employed and is required to be higher than the solidifying point of the indole mixture, and the temperature typically ranges from about 10° C. to about 150° C. and preferably ranges from about 50° C. to 120° C. The temperatures of higher than 150° C. are in some cases above the boiling points of the desorbents A and B and, in addition, requires a large amount of heating energy and thus uneconomical.

The following Examples are given to illustrate the present invention more specifically. However, it should be understood that the invention is in no way limited to these specific embodiments. In these Examples and Comparative Examples, the adsorption capacity W is denoted by the formula;

$W$(mg/g-zeolite) =

-continued $$\frac{\left[\begin{array}{l}\text{Weight of solute}\\ \text{before adsorption (mg)}\end{array}\right] - \left[\begin{array}{l}\text{Weight of solution in liquid}\\ \text{phase equilibrated with}\\ \text{zeolite phase after adsorption (mg)}\end{array}\right]}{\text{Weight of zeolite after calcination (g)}}$$

The rate of desorption of indole D is a rate of indole which is desorbed from the zeolite by the addition of acetonitrile as a desorbent having a strong adsorbability and is denoted by the formula;

$$D\;(\%) = \frac{\text{Weight of indole desorbed from zeolite after addition of acetonitrile}}{\text{Weight of indole adsorbed on zeolite before addition of acetonitrile}} \times 100$$

The degree of concentration is denoted by the formula;

$$\begin{array}{l}\text{Degree of}\\ \text{concentration (\%)}\end{array} = \frac{\text{Weight of indole in effluent}}{\text{Weight of indole plus others in indole effluent}} \times 100$$

The faujasite structured zeolites used in the Examples are commercially available X type zeolite and Y type zeolite having a particle diameter of 80 to 120 mesh (Tyler standard sieve) and Na ions as the metal ions (manufactured by Nikka Seiko Kabushiki Kaisha).

EXAMPLE 1

In a gloved box field with nitrogen gas, 1 g of the commercially available X type zeolite powder which had been calcined at 500° C. for 2 hours and cooled in a desiccator was contacted with 2 g of a mixed solution containing 5.3% by weight of 2-methylnaphthalene, 5.2% by weight of indole and 89.5% by weight of toluene as the diluent at 70° C. for 2 hours.

When the selectivity was calculated from the change in the composition of 2-methylnaphthalene and indole, $K_{2\text{-methylnaphthane}}^{indole}$ was 98 and W was 96.5 mg/g-zeolite.

Then to the above described mixed solution was added 0.5 g of acetonitrile, and the contact with the zeolite was conducted at 70° C. for 2 hours. From the desorbed amount of indole, D was calculated to find 95.3%.

EXAMPLE 2 & COMPARATIVE EXAMPLES 1 TO 3

By using the commercially available Y type zeolite and commercially available A type zeolites 3A, 4A and 5A having a particle distribution of 80 to 120 mesh, $K_{2\text{-methylnaphthalene}}^{indole}$ and W were measured in the same manner as in Example 1 and D was measured with the commercially available Y type zeolite. The results are shown in Table 1.

TABLE 1

| Example No. | Adsorbent | $K_{2\text{-methylnaphthane}}^{indole}$ | W (mg/g-zeolite) | D (%) |
|---|---|---|---|---|
| 2 | Commercially available Y type zeolite | 110 | 86.9 | 100 |
| Comparative Example 1 | Commercially available A type zeolite 3A | 1.00 | 1.1 | — |
| 2 | Commercially available A type zeolite 4A | 1.01 | 1.3 | — |
| 3 | Commercially available A type zeolite 5A | 1.01 | 1.5 | — |

EXAMPLES 3 AND 4

The procedures of Example 1 were repeated except that a mixed solution containing 6.0% by weight of biphenyl, 6.0% by weight of indole and 88.0% by weight of toluene as the diluent was employed instead of the mixed solution and that the commercially available Y type was also employed. $K_{biphenyl}^{indole}$ and W measured are shown in Table 2.

TABLE 2

| Example No. | Adsorbent | $K_{biphenyl}^{indole}$ | W (mg/g-zeolite) |
|---|---|---|---|
| 3 | Commercially avaiable X type zeolite | 105 | 86.6 |
| 4 | Commerically available Y type zeolite | 116 | 78.1 |

EXAMPLES 5 TO 20

The ion-exchange sites located on the commercially available X type zeolite were replaced by the metal ion as set forth in Table 3 by treating the X type zeolite with an aqueous nitrate or hydrochlorate solution of the metal ion whose ion concentration was about 2 N, at 70° C. for 4 hours three times, and then the ion-exchanged zeolite was washed sufficiently with water and dried at 90° C. for 6 hours. The zeolite thus obtained was calcined at 500° C. for 2 hours and cooled in a disiccator. In the same manner as in Example 1, $K_{2\text{-methylnaphthalene}}^{indole}$ W and D were measured and the results are shown in Table 3.

TABLE 3

| Example No. | Exchanged Metal Ion | $K_{2\text{-methylnaphthalene}}^{indole}$ | W (mg/g-zeolite) | D (%) |
|---|---|---|---|---|
| 5 | Li | 85 | 95.4 | 96.1 |
| 6 | K | 103 | 106 | 92.8 |
| 7 | Rb | 95 | 86.7 | 88.3 |
| 8 | Cs | 91 | 78.5 | 89.4 |
| 9 | Mg | 110 | 98.6 | 81.1 |
| 10 | Ca | 107 | 95.1 | 75.0 |
| 11 | Sr | 81 | 85.8 | 78.2 |
| 12 | Ba | 75 | 75.8 | 64.7 |
| 13 | Cu | 63 | 65.9 | 66.6 |
| 14 | Ag | 82 | 72.3 | 71.3 |
| 15 | Zn | 91 | 105 | 67.2 |
| 16 | Cd | 96 | 101 | 63.9 |
| 17 | Fe | 64 | 74.3 | 56.1 |
| 18 | Co | 76 | 83.7 | 60.4 |
| 19 | Ni | 78 | 76.9 | 59.7 |
| 20 | La | 98 | 110 | 73.5 |

EXAMPLE 21 TO 36

The ion-exchange of the commercially available Y type zeolite was conducted in the same manner as in Examples 5 to 20, and $K_{2\text{-methylnaphthalene}}^{indole}$ W and D were measured in the same manner as in Example 1 with the results as set forth in Table 4.

TABLE 4

| Example No. | Exchanged Metal Ion | $K^{indole}_{2-methylnaphthalene}$ | W (mg/g-zeolite) | D (%) |
|---|---|---|---|---|
| 21 | Li | 103 | 81.9 | 99.5 |
| 22 | K | 114 | 96.3 | 100 |
| 23 | Rb | 82 | 86.1 | 98.7 |
| 24 | Cs | 85 | 72.2 | 97.4 |
| 25 | Mg | 106 | 102 | 85.8 |
| 26 | Ca | 113 | 101 | 73.1 |
| 27 | Sr | 76 | 92.1 | 81.4 |
| 28 | Ba | 78 | 90.2 | 87.4 |
| 29 | Cu | 51 | 63.5 | 69.2 |
| 30 | Ag | 67 | 74.7 | 72.0 |
| 31 | Zn | 69 | 117 | 68.7 |
| 32 | Cd | 84 | 104 | 70.7 |
| 33 | Fe | 67 | 72.1 | 69.3 |
| 34 | Co | 76 | 97.4 | 75.7 |
| 35 | Ni | 91 | 97.9 | 68.0 |
| 36 | La | 120 | 98.5 | 83.6 |

EXAMPLES 37 TO 46

In a gloved box filled with nitrogen gas, 1 g of the commercially available X type zeolite or Y type zeolite powder which had been calcined at 500° C. for 2 hours and cooled in a desiccator and whose ion-exchangeable sites had been replaced by Li, Na, K, Rb or Cs was contacted with 1 g of toluene at 70° C. for 2 hours and then a mixed solution containing 10% by weight of indole and 90% by weight of toluene was added thereto. Starting from this time as zero hour the change in the amount of indole adsorbed on the zeolite with the passage of time was measured. In FIG. 1, the adsorbed amount of indole with the passage of time, C, divided by the adsorbed amount of indole after a sufficient period of time, i.e., at least 3 hours had passed, C∞, is plotted against the time measured. The meaning of the curves in FIGS. 1 and 2 is shown in Table 5.

TABLE 5

Figure 2:
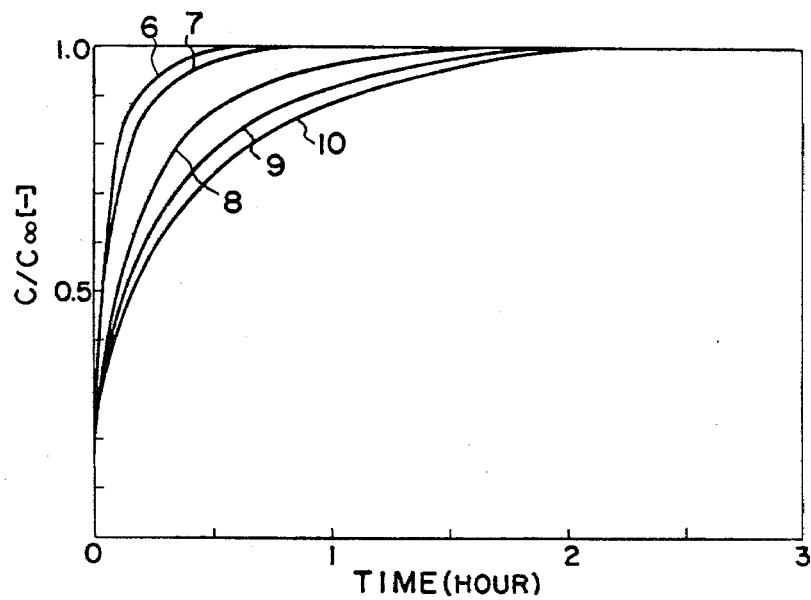

| FIG. No. | Example No. | Curve No. | Exchanged Metal Ion |
|---|---|---|---|
| FIG. 1 | 37 | 1 | X Type Zeolite Li |
|  | 38 | 2 | Na(commercially available X type zeolite) |
|  | 39 | 3 | K |
|  | 40 | 4 | Rb |
|  | 41 | 5 | Cs |
| FIG. 2 | 42 | 6 | Y Type Zeolite Li |
|  | 43 | 7 | Na(commercially available Y type zeolite) |
|  | 44 | 8 | K |
|  | 45 | 9 | Rb |
|  | 46 | 10 | Cs |

From FIGS. 1 and 2, it can be understood that the adsorption velocity is remarkably high with the Li ion- or Na ion- replaced Y type zeolite compared with the other zeolites.

EXAMPLE 47 TO 56

In a gloved box filled with nitrogen gas, 1 g of Li ion-replaced Y type zeolite powder was contacted with 2 g of a mixed solution containing 5.0% by weight of indole, 5.0% by weight of a desorbent A as set forth in Table 6 and 90.0% by weight of toluene as the diluent at 70° C. for 2 hours. The selectivity $K^{indole}_{desorbentA}$ was calculated from the change in the composition of indole and the desorbent. The results are shown in Table 6.

TABLE 6

| Example No. | Desorbent A | $K^{indole}_{desorbent A}$ |
|---|---|---|
| 47 | Isopropyl ether | 5.8 |
| 48 | Di-n-butyl ether | 9.5 |
| 49 | Anisole | 1.8 |
| 50 | Ethyl acetate | 0.41 |
| 51 | n-Butyl acetate | 0.68 |
| 52 | Isoamyl acetate | 0.72 |
| 53 | Methyl ethyl ketone | 0.20 |
| 54 | Methyl isobutyl ketone | 0.62 |
| 55 | 2-Octanone | 1.4 |
| 56 | Cyclohexanone | 0.33 |

EXAMPLE 57

A perpendicularly cylindrical glass column having a diameter of 8 mm and a length of 1,000 mm was packed with the commercially available X type zeolite to a packed height of 950 mm. While the temperature of the column was maintained at 70° C., anisole was fed to one end of the column at a rate of 0.5 ml per minute to fill the column with anisole. When anisole started flowing from the other end of the column, the feed of anisole was stopped and 11.0 g of a mixed solution containing 40% by weight of 2-methylnaphthalene, 10% by weight of indole and 50% by weight of toluene was fed to the column at a rate of 0.5 ml per minute and anisole was fed again to the column at a rate of 0.5 ml per minute until 2-methylnaphthane and indole were eluted from the column and the effluent was collected in 1 to 3 ml fractions per minute, which was then subjected to analysis.

Figure 3:
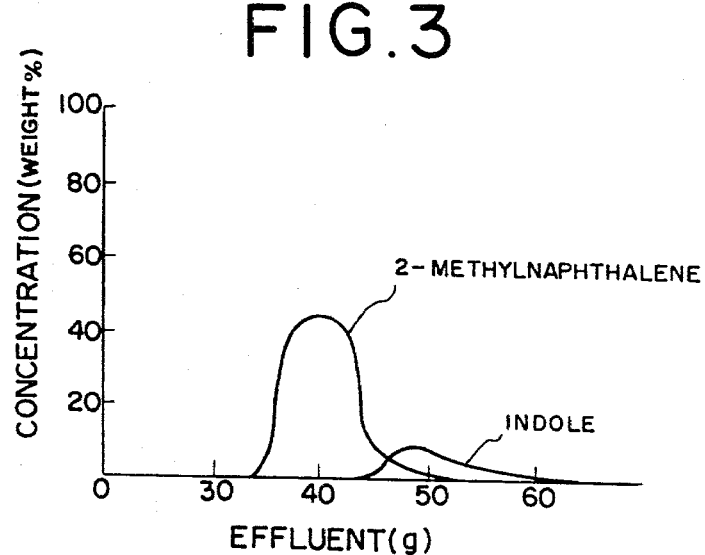
FIGS. 3 to 16 illustrate the relationship between the weight of the effluent collected and the concentration of each substance in the effluent in the adsorption separation of the indole mixture by using a faujasite structured zeolite packed into a column in the Examples and Comparative Examples according to this invention.

In FIG. 3, the concentration of the 2-methylnaphthalene and indole in the effluent is plotted against the weight of the effluent collected, starting from the introduction of the mixed solution as zero gram. From FIG. 3, it is understood that the separation of indole from 2-methylnaphthalene occurred.

EXAMPLE 58

The procedures of Example 57 were repeated except that the commercially available Y type zeolite instead of the commercially available X type zeolite and a mixture of 97% by weight of 1-methylnaphthalene and 3% by weight of indole instead of the mixed solution containing 40% by weight of 2-methylnaphthalene, 10% by weight of indole and 50% by weight of toluene were employed and that the temperature of the column was maintained at 90° C.

Figure 4:
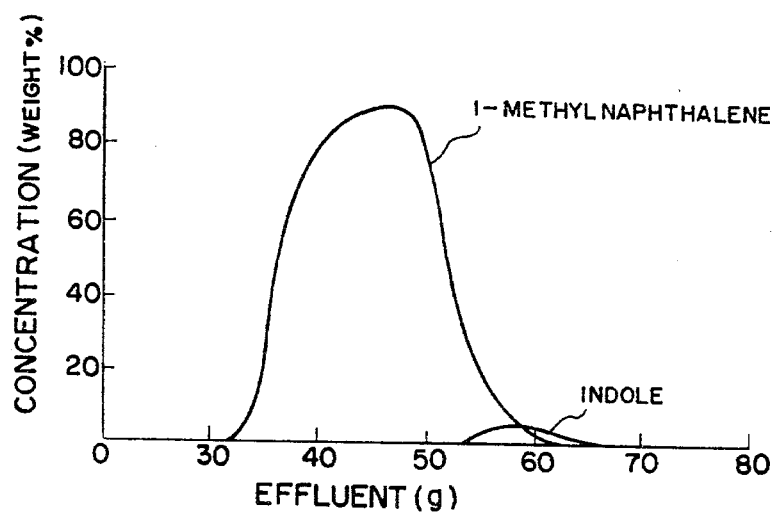

In FIG. 4,, the concentration of the 1-methylnaphthalene and indole in the effluent is plotted against the weight of the effluent collected. From FIG. 4 it is understood that the separation of indole from 1-methylnaphthalene occurred.

EXAMPLE 59

The same column as in Example 57 was packed with Li ion-replaced Y type zeolite and the temperature of the column was maintained at 70° C. To one end of the column was fed n-butyl acetate at a rate of 0.5 ml per minute to fill the column with n-butyl acetate. Then 25.8 g of a mixed solution containing 40% by weight of 2-methylnaphthane, 10% by weight of indole and 50% by weight of toluene were fed to the column at a rate of 0.5 ml per minute and subsequently n-butyl acetate was again fed to the column at a rate of 0.5 ml per minute.

Figure 5:
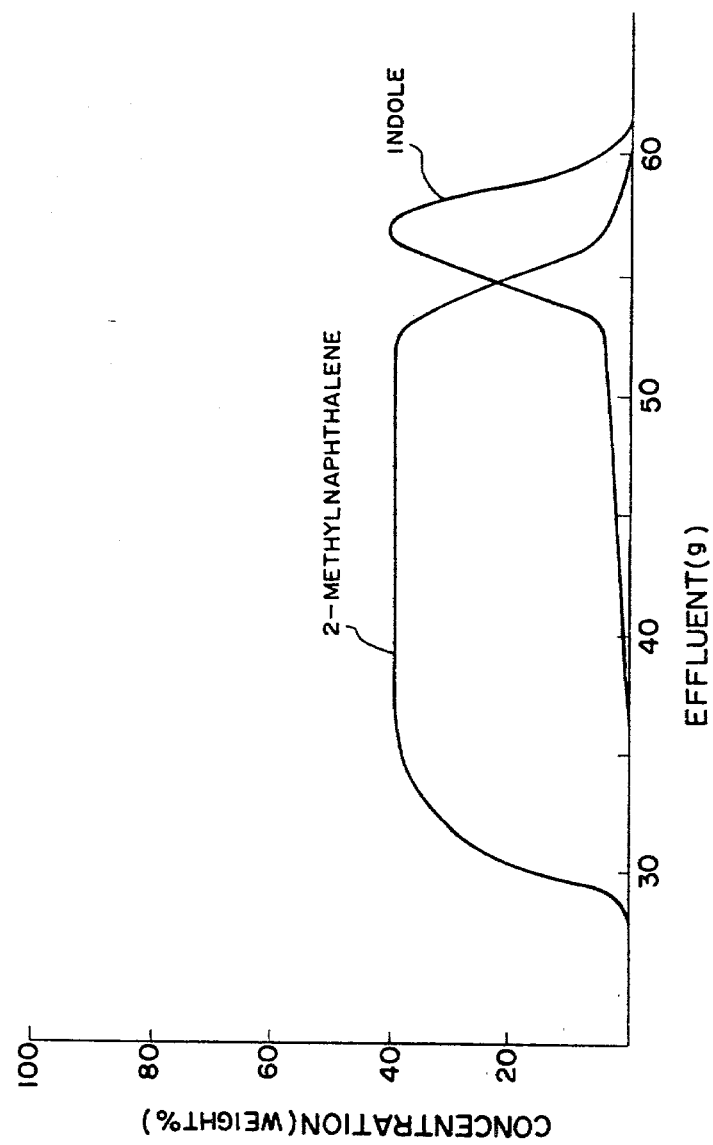

In FIG. 5, the concentration of the 2-methylnaphthalene and indole in the effluent is plotted against the weight of the effluent. From FIG. 5 it is understood that the separation of indole from 2-methylnaphthalene occured.

EXAMPLE 60

The same column as in Example 57 was packed with Li-replaced Y type zeolite and the temperature of the column was maintained at 70° C. To one end of the column was fed anisole at a rate of 0.5 ml per minute to fill the column with anisole. Then 22.0 g of a mixed solution of toluene and a coal tar distillate having a boiling point of 220° C. to 270° C. which had been washed with 10% by weight sulfuric acid and then with 10% by weight aqueous sodium hydroxide solution were fed to the column at a rate of 0.5 ml. The composition of the mixed solution was as follows:

| Naphthalene | 19.4 (weight %) |
| Thionaphthene | 0.8 |
| 1-Methylnaphthalene | 3.7 |
| 2-Methylnaphthalene | 5.7 |
| Biphenyl | 1.0 |
| 1,5-Dimethylnaphthalene | 0.5 |
| 1,7-Dimethylnaphthalene | 1.4 |
| 2,6-Dimethylnaphthalene | 0.9 |
| Indole | 1.6 |
| Acenaphthene | 3.1 |
| Diphenylene oxide | 2.3 |
| Fluorene | 0.9 |
| Toluene | 56.4 |
| Others | 2.3 |

Then anisole was fed again at a rate of 0.5 ml until the above described substances to be separated were eluted from the column and the effluent was collected in 1 to 3 ml fractions per minute, which was subjected to analysis.

Figure 6:
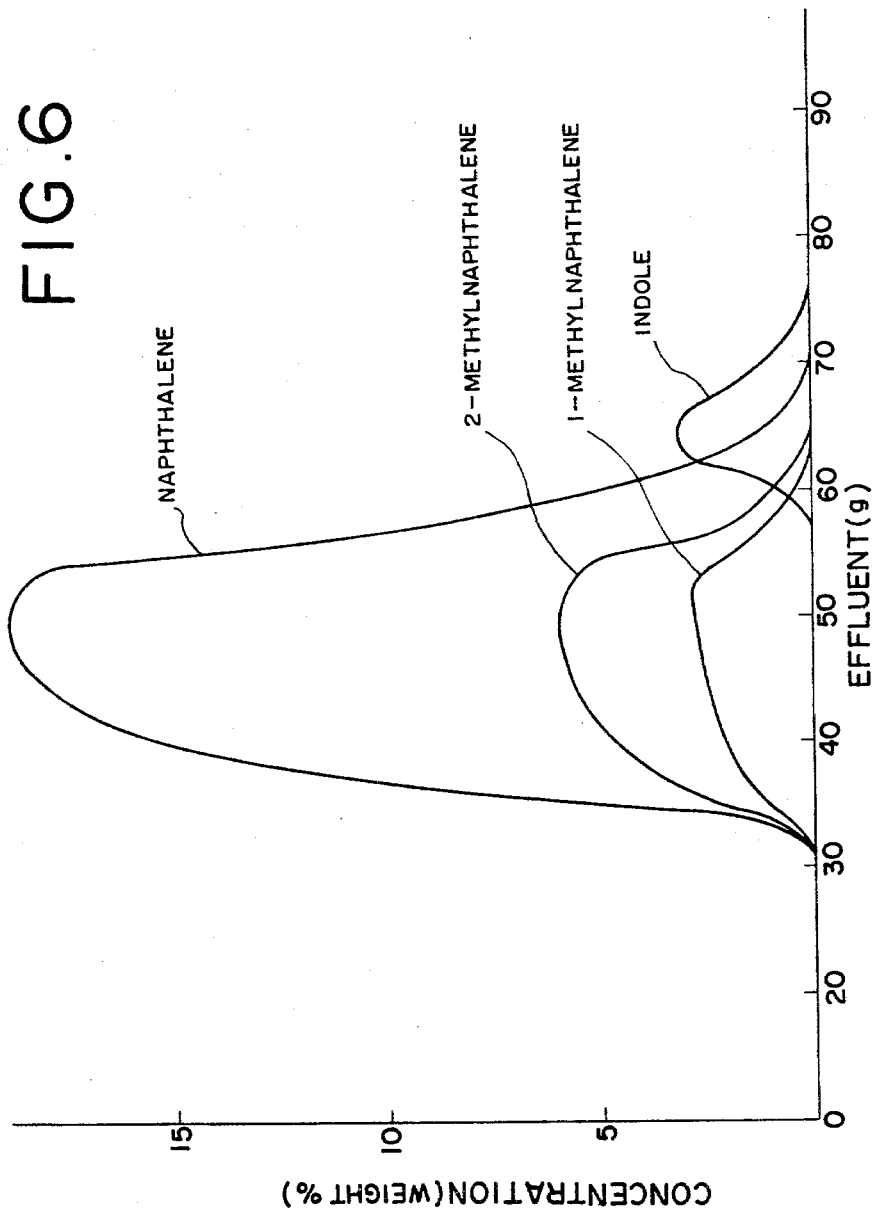
Figure 7:
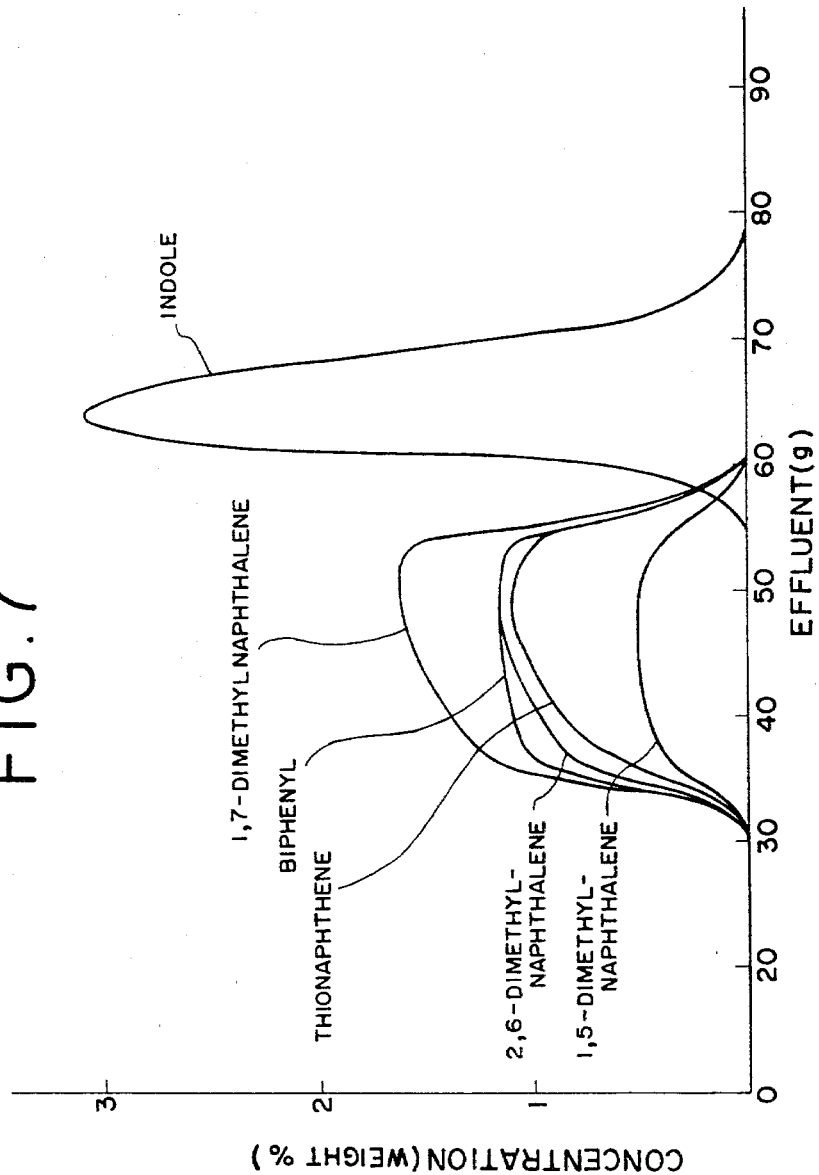
Figure 8:
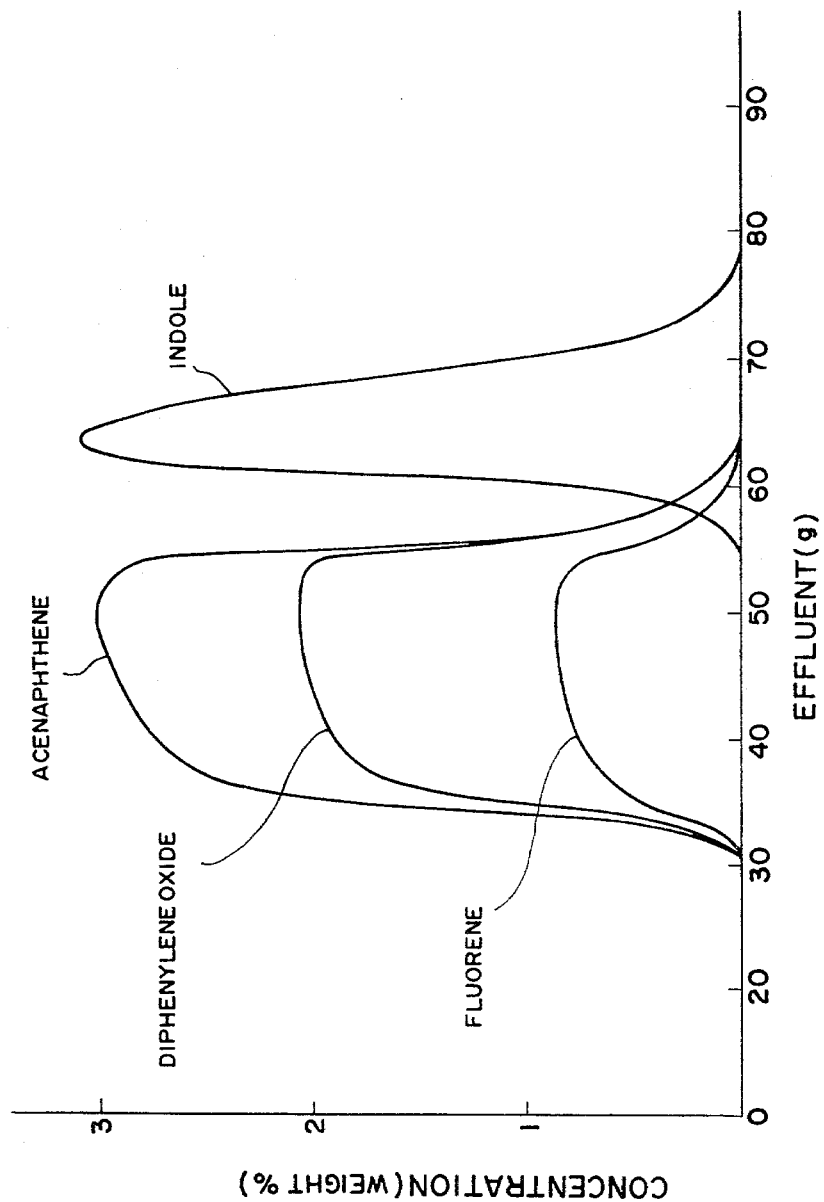

In FIGS. 6, 7 and 8, the concentration of the substances in the effluent is plotted against the weight of the effluent collected. From FIGS. 6, 7 and 8, it is understood that the separation of indole from the other substances.

EXAMPLE 61

The same column as in Example 57 was packed with Li ion-replaced zeolite in the same manner as in Example 57. While the temperature of the column was maintained at 70° C. anisole was fed, as the desorbent (A), to one end of the column at a rate of 0.5 ml per minute to fill the column with anisole. When anisole started flowing from the other end of the column, the feed of anisole was stopped and 15.0 g of a mixture of 97% by weight of 1-methylnaphthalene and 3% by weight of indole were fed to the column at a rate of 0.5 ml per minute and then 20 g of toluene as the desorbent (B) were fed to the column at a rate of 0.5 ml per minute and subsequently anisole was fed again to the column at a rate of 0.5 ml per minute until indole was eluted from the column.

Figure 9:
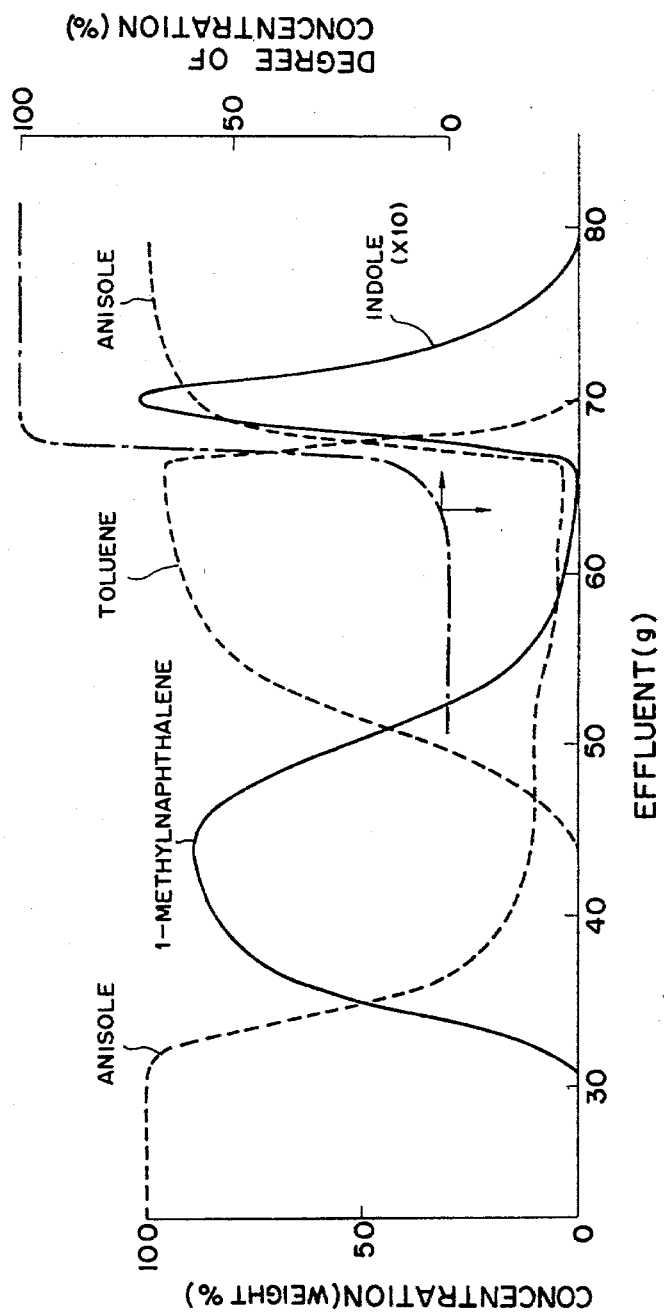

In FIG. 9, the concentration of the 1-methylnaphthalene and indole in the effluent and the degree of concentration are plotted against the weight of the effluent collected. From FIG. 9 it is understood that the degree of concentration reached almost 100% in the concentrated portion.

EXAMPLES 62 TO 64

The procedures of Example 61 were repeated except that the desorbent B as described in Table 7 was employed instead of the toluene and that the amount of the mixture as described in Table 7 was employed.

TABLE 7

| Example No. | Desorbent B (g) | Mixture (g) | Result (FIG. No.) |
|---|---|---|---|
| 62 | Ethylbenzene 25.0 | 19.0 | 10 |
| 63 | p-Xylene 25.0 | 20.8 | 11 |
| 64 | Isopropylbenzene 25.0 | 20.3 | 12 |

Figure 10:
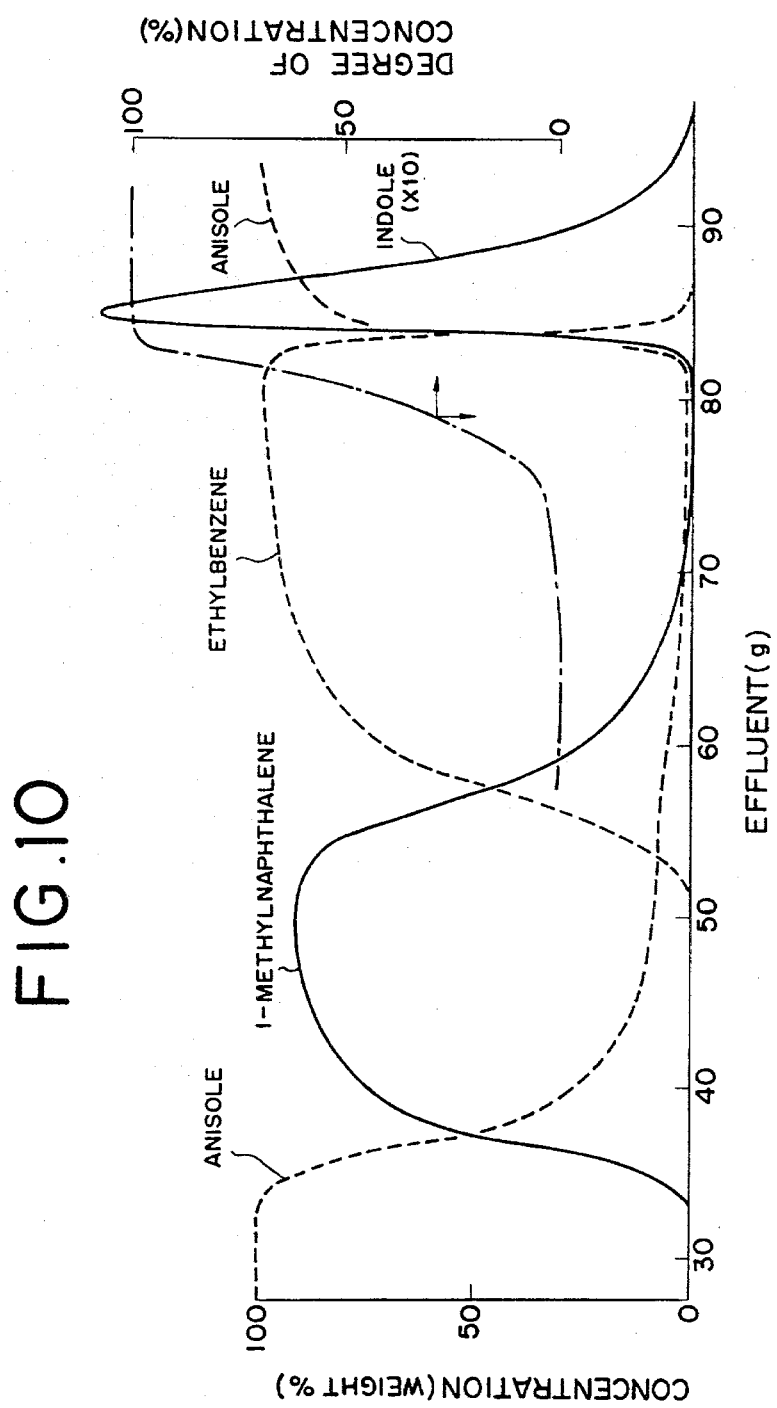
Figure 11:
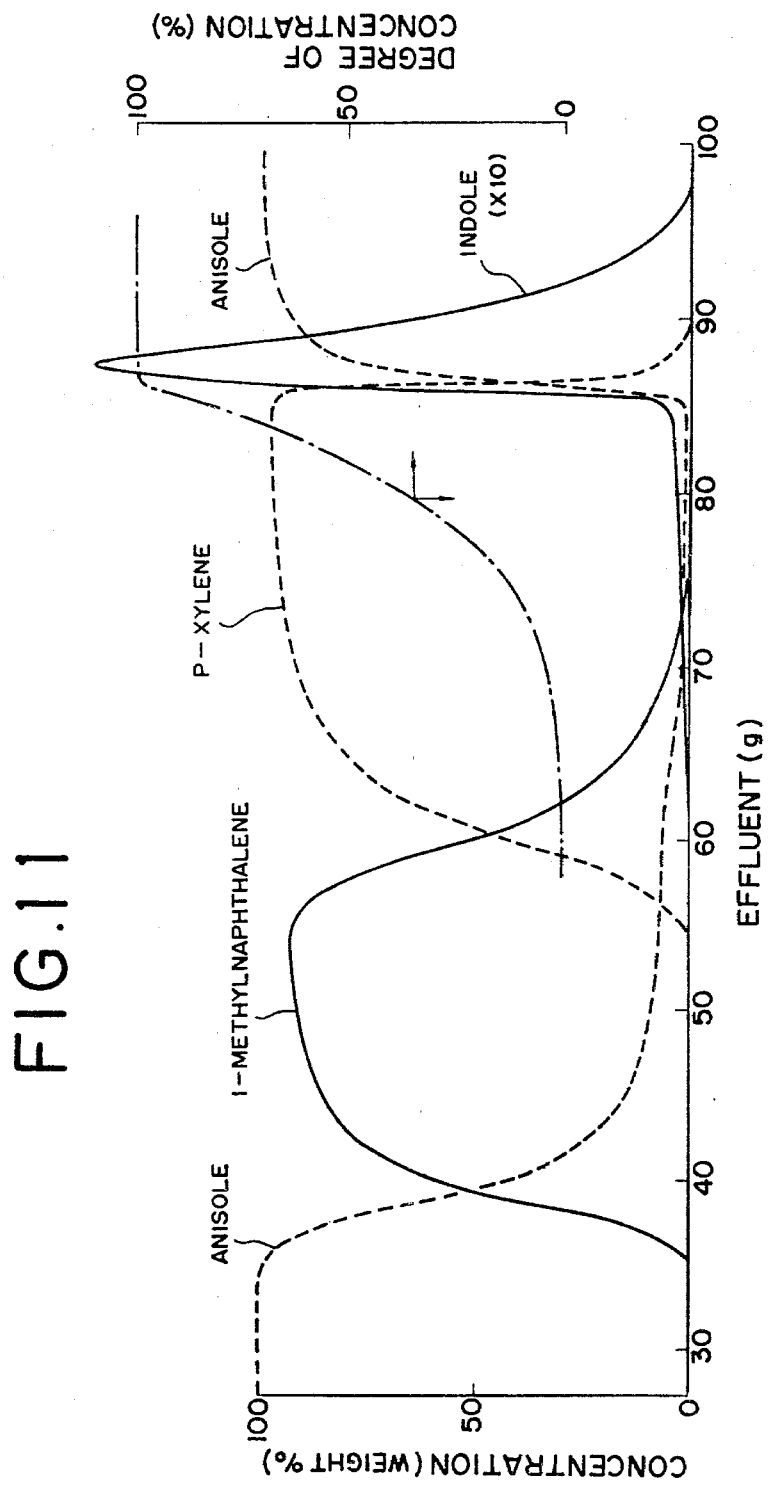
Figure 12:
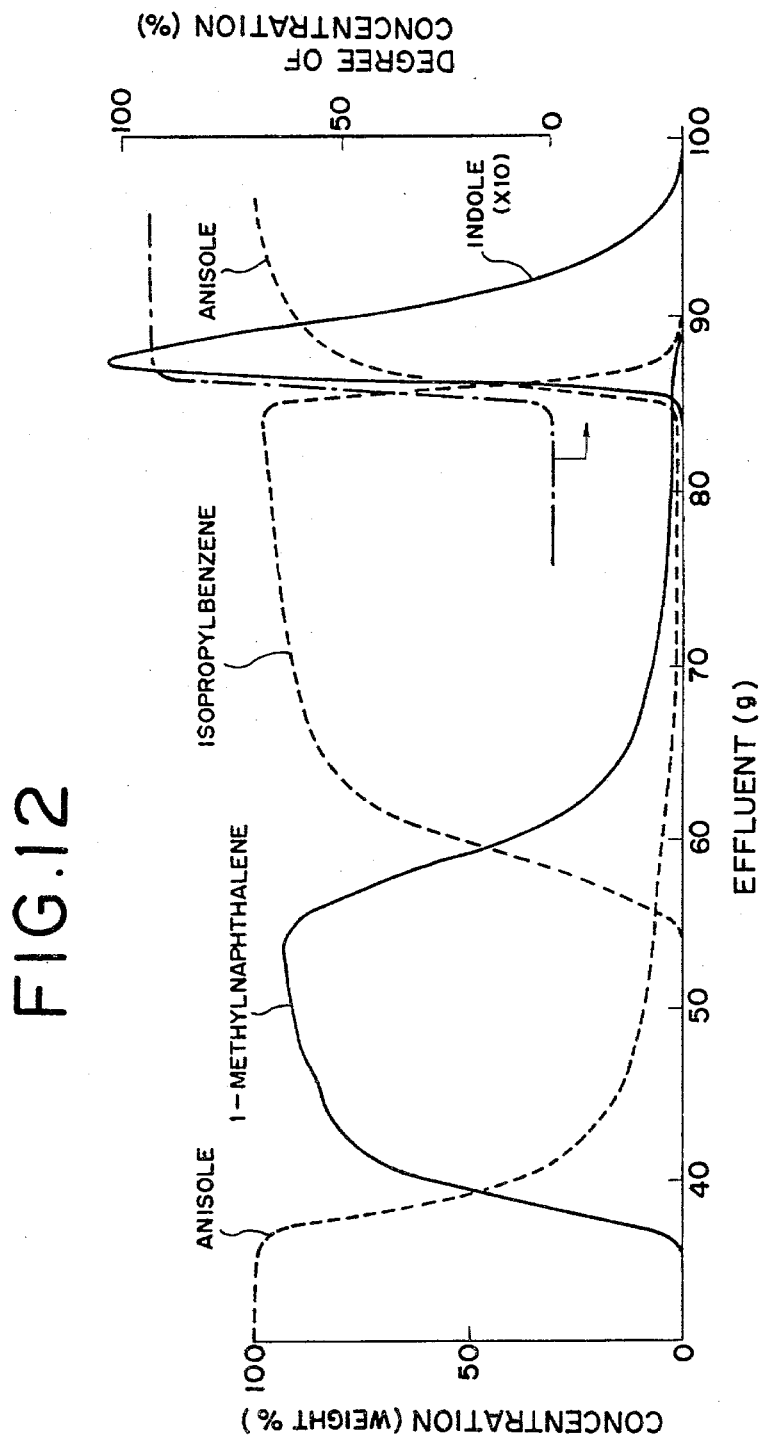

From FIGS. 10, 11 and 12, it is undestood that indole having a high purity was separated.

EXAMPLE 65

The procedures of Example 61 were repeated except that 15.7 g of a coal tar distillate having the following composition and a boiling point of 220° C. to 270° C. which had been washed with 10% by weight sulfuric acid and then with 10% by weight aqueous sodium hydroxide solution were employed instead of the mixture and that 19.1 g of toluene were employed instead of 20 g of toluene.

| Composition of Coal Tar | |
|---|---|
| Naphthalene | 7.9 (weight %) |
| Thionaphthene | 1.5 |
| 1-Methylnaphthalene | 14.4 |
| 2-Methylnaphthalene | 39.2 |
| Biphenyl | 7.9 |
| 1,5-Dimethylnaphthalene | 3.4 |
| 1,7-Dimethylnaphthalene | 5.7 |
| 2,6-Dimethylnaphthalene | 4.2 |
| Indole | 3.6 |
| Acenaphthene | 5.6 |
| Diphenylene oxide | 4.1 |
| Fluorene | 0.4 |
| Others | 2.1 |

Figure 13:
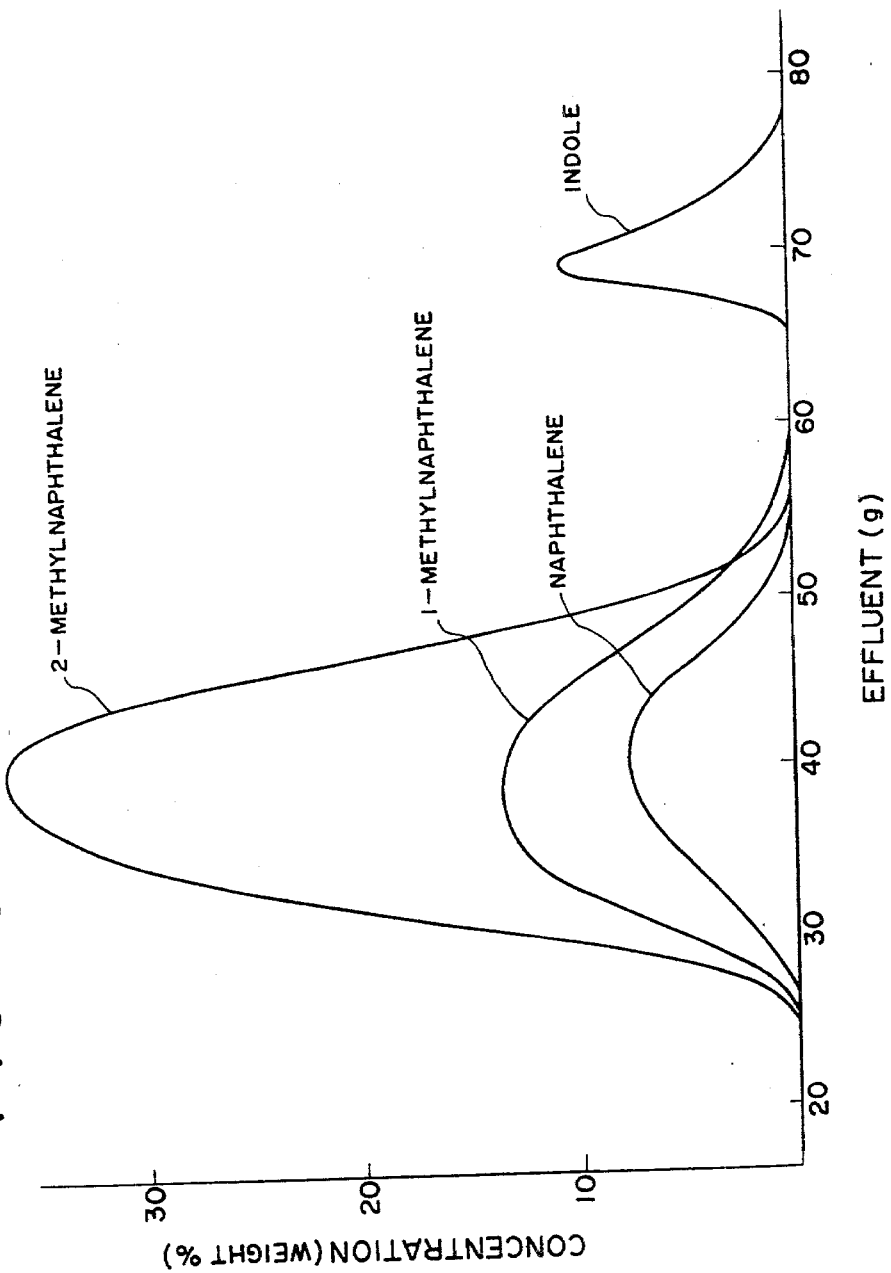
Figure 14:
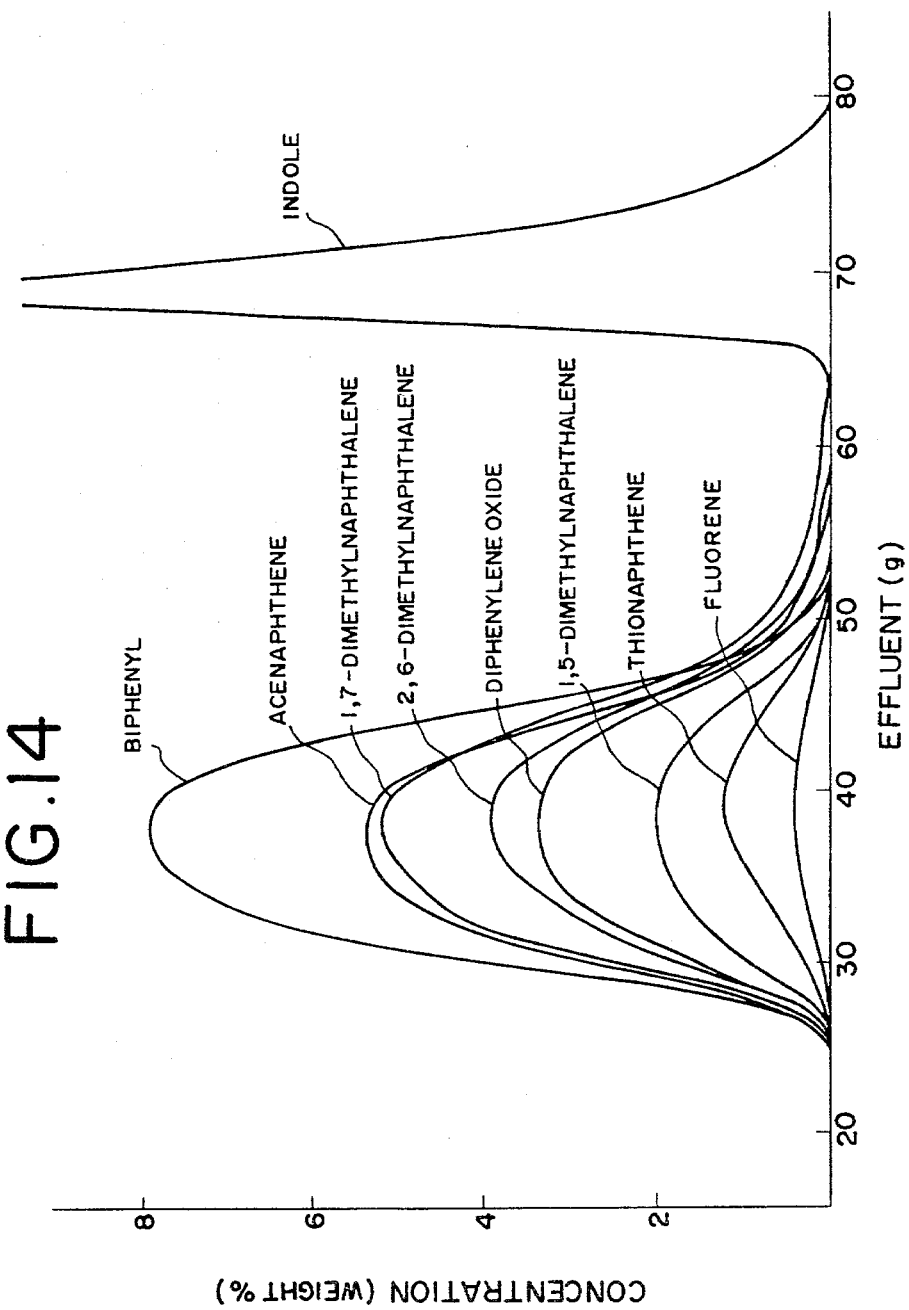

In FIGS. 13 and 14, the concentration of the substances to be separated in the effluent is plotted against the weight of the effluent collected but the effluent curves of toluene and anisole are omitted. From FIGS. 13 and 14 it is understood that the separation of indole from the other substances occurred.

COMPARATIVE EXAMPLE 4

Figure 15:
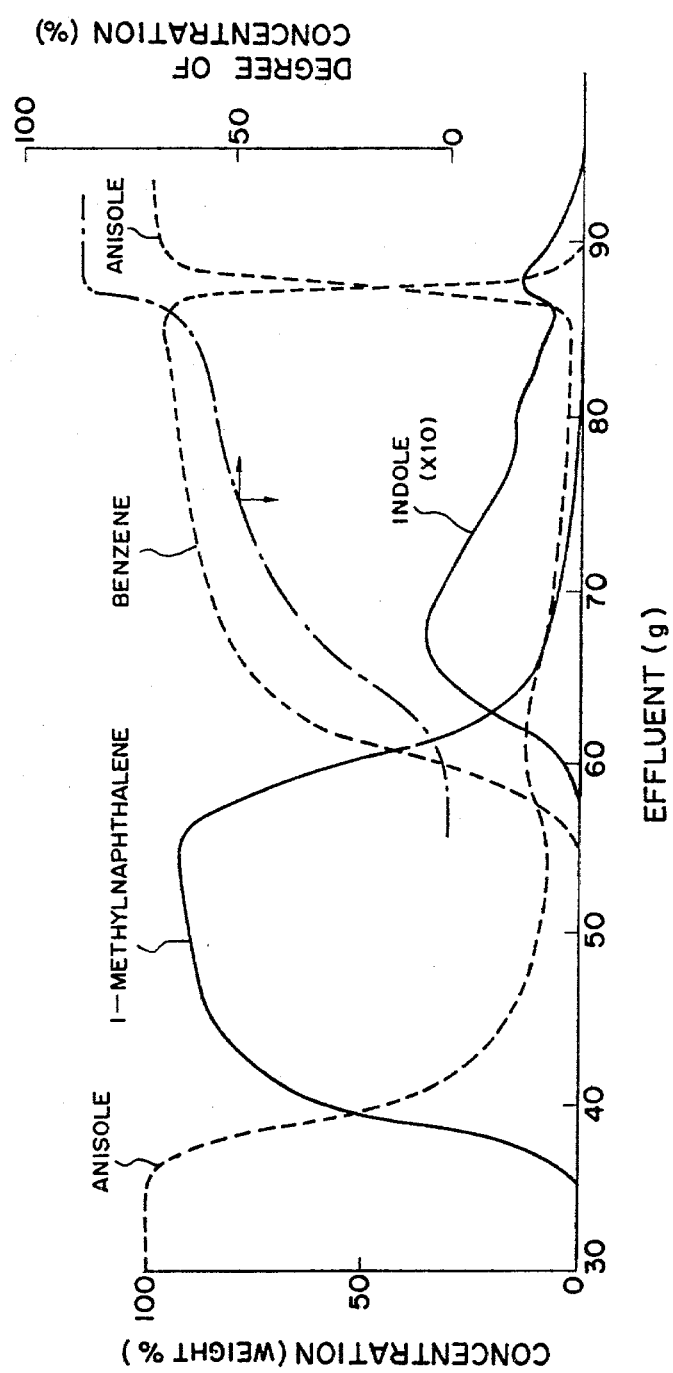

The procedures of Example 61 were repeated except that 20.2 g of the mixture were employed instead of 15.0 g of the mixture and that 25.5 g of benzene were employed as the desorbent B instead of the toluene. The result is shown in FIG. 15. From FIG. 15 it is understood that almost all the indole was desorbed by the benzene.

COMPARATIVE EXAMPLE 5

Figure 16:
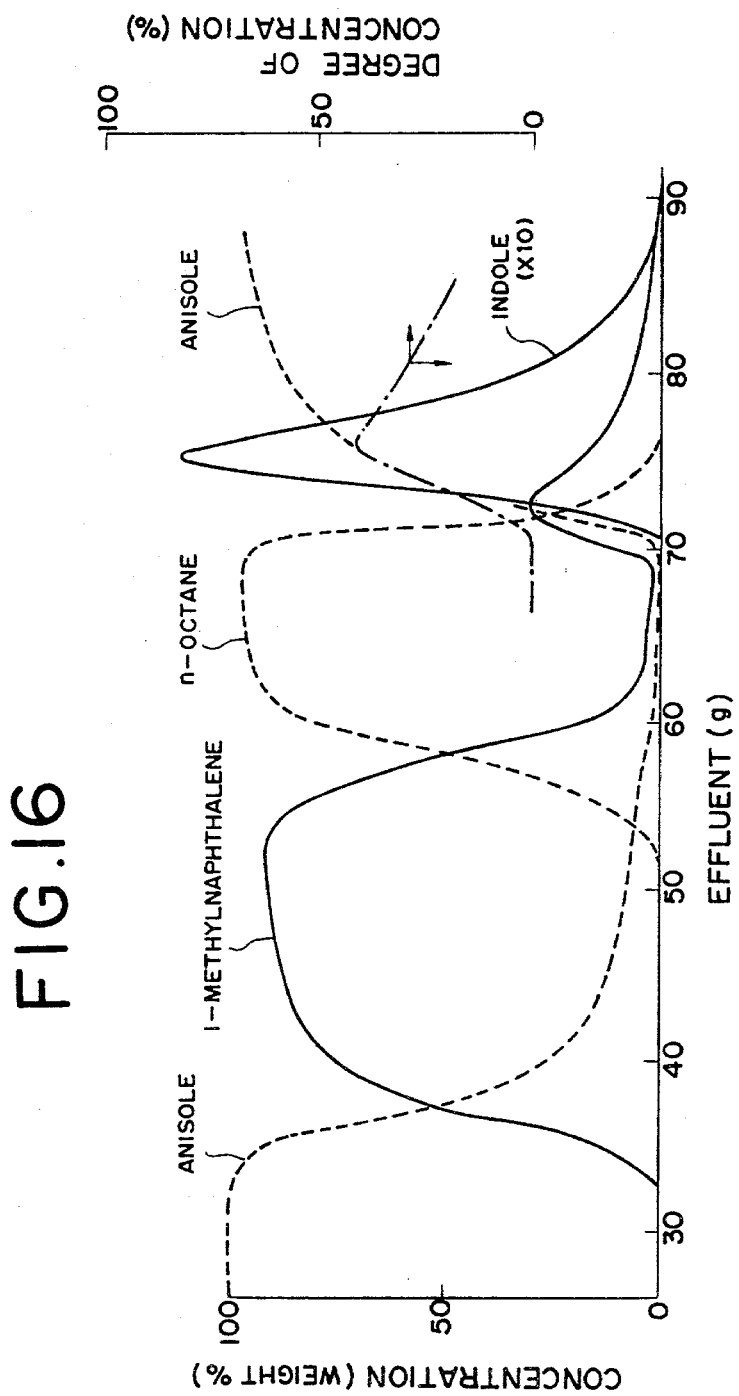

The procedures of Example 61 were repeated except that 21.9 g of the mixture were employed instead of the mixture and that 19.4 g of n-octane were employed as the desorbent B instead of the toluene. The result is shown in FIG. 16. From FIG. 16 it is understood that a remarkable amount of 1-methylnaphthalene was eluted in the concentrated portion.

What is claimed is:

1. A process for separating indole from a mixture of indole with at least one compound selected from the group consisting of naphthalene, thionaphthene, 1-methylnaphthalene, 2-methylnaphthalene, biphenyl, 1,5-dimethylnaphthalene, 2,6-dimethylnaphthalene, acenaphthene, diphenylene oxide and fluorene which comprises the step of contacting the mixture with an X type zeolite whose exchangeable cation sites are occupied by at least one cation selected from the group consisting of lithium, sodium, potassium, rubidium, cesium, magnesium, calcium, strontium, barium, copper, silver, zinc, cadmium, iron, nickel, cobalt and lanthanum ions or a Y type zeolite whose exchangeable cation sites are occupied by at least one cation selected from the group consisting of lithium, sodium, potassium, rubidium, cesium, magnesium, calcium, strontium, barium, copper, silver, zinc, cadmium, iron, nickel, cobalt and lanthanum ions to selectively adsorb indole on the zeolite and contacting a desorbent A selected from the group consisting of $C_{2-10}$ aliphatic ethers, $C_{7-10}$ aromatic ethers, $C_{2-10}$ aliphatic esters and $C_{3-10}$ aliphatic ketones, with the indole-adsorbed zeolite to separate indole, the selectivity of the zeolite for indole over the desorbent A represented by K indole desorbent A ranging from 0.1 to 10.

2. A process according to claim 1, including the step of contacting at least one desorbent B of the formula,

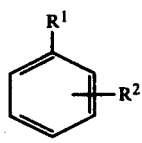

wherein
R$^1$ is a C$_{1-3}$ alkyl group, and
R$^2$ is a hydrogen atom or a C$_{1-3}$ alkyl group, with the indole-adsorbed zeolite prior to the contact of the desorbent A with the indole-adsorbed zeolite.

3. A process according to claim 1 or 2, wherein the mixture is contacted with an X type zeolite whose exchangeable cation sites are occupied by at least one cation selected from the group consisting of lithium, sodium, potassium, rubidium and cesium ions.

4. A process according to claim 1 or 2, wherein the mixture is contacted with a Y type zeolite whose exchangeable cation sites are occupied by at least one cation selected from the group consisting of lithium, sodium, potassium, rubidium and cesium ions.

5. A process according to claim 1 or 2, wherein the mixture is contacted with a Y type zeolite whose exchangeable cation sites are occupied by lithium ions.

6. A process according to claim 1 or 2, wherein the mixture is contacted with a Y type zeolite whose exchangeable cation sites are occupied by sodium ions.

7. A process according to claim 1 or 2, wherein the indole-containing mixture is a distillate of coal tar having a boiling point of 220° C. to 270° C. obtained by distilling coal tar.

8. A process according to claim 1 or 2, wherein the indole-containing mixture is an oily substance obtained by washing with an acid and a base a distillate of coal tar having a boiling point of 220° C. to 270° C.

9. A process according to claim 1 or 2, wherein the desorbent A is selected from the group consisting of diethyl ether, di-n-propyl ether, isopropyl ether, methyl n-butyl ether, ethyl n-butyl ether, di-n-butyl ether, anisole, ethyl acetate, n-propyl acetate, n-butyl acetate, n-amyl acetate, isobutyl acetate, tert-butyl acetate, isoamyl acetate, methyl propionate, ethyl propionate, di-n-propyl ketone, methyl ethyl ketone, methyl isobutyl ketone, 2-pentanone, 2-heptanone, 2-octanone and cyclohexanone.

10. A process according to claim 1 or 2, wherein the desorbent A is selected from the group consisting of isopropyl ether, di-n-butyl ether, anisole, ethyl acetate, n-butyl acetate, isoamyl acetate, methyl ethyl ketone, methyl isobutyl ketone and cyclohexanone.

11. A process according to claim 1 or 2, wherein the desorbent A is anisole.

12. A process according to claim 2, wherein desorbent B is at least one compound selected from the group consisting of toluene, ethylbenzene, o-xylene, m-xylene, p-xylene and isopropylbenzene.

* * * * *